US012393571B2

(12) United States Patent
Shultis et al.

(10) Patent No.: US 12,393,571 B2
(45) Date of Patent: Aug. 19, 2025

(54) MULTIDIMENSIONAL MULTITENANT SYSTEM

(71) Applicant: Humana Inc., Louisville, KY (US)

(72) Inventors: Jonathan C. Shultis, Mountain View, CA (US); Mark J. Willard, Rancho Santa Fe, CA (US)

(73) Assignee: Humana Inc., Louisville, KY (US)

( * ) Notice: Subject to any disclaimer, the term of this patent is extended or adjusted under 35 U.S.C. 154(b) by 105 days.

(21) Appl. No.: 16/211,166

(22) Filed: Dec. 5, 2018

(65) Prior Publication Data

US 2020/0183916 A1  Jun. 11, 2020

(51) Int. Cl.
*G06F 16/23* (2019.01)
*G06F 21/62* (2013.01)
*G16H 10/60* (2018.01)

(52) U.S. Cl.
CPC .......... *G06F 16/2379* (2019.01); *G06F 21/62* (2013.01); *G16H 10/60* (2018.01); *G06F 21/6245* (2013.01)

(58) Field of Classification Search
CPC .. G06F 16/2379; G06F 21/62; G06F 21/6245; G16H 10/60
USPC .......................................................... 707/736
See application file for complete search history.

(56) References Cited

U.S. PATENT DOCUMENTS

| | | | |
|---|---|---|---|
| 2006/0235831 A1* | 10/2006 | Adinolfi | G06Q 40/00 |
| 2008/0162544 A1* | 7/2008 | Weissman | G06F 16/211 |
| 2010/0205227 A1* | 8/2010 | Weissman | G06Q 10/063112 |
| | | | 707/803 |
| 2011/0106808 A1* | 5/2011 | Hersans | G06F 16/90328 |
| | | | 707/740 |
| 2011/0219046 A1* | 9/2011 | Nesmyanovich | G06F 16/00 |
| | | | 707/812 |
| 2011/0264704 A1* | 10/2011 | Mehra | G06F 16/289 |
| | | | 707/802 |
| 2011/0302212 A1* | 12/2011 | Agrawal | G06F 11/3636 |
| | | | 707/805 |
| 2013/0031496 A1* | 1/2013 | Mathrubootham | G06F 3/048 |
| | | | 715/764 |
| 2013/0238641 A1* | 9/2013 | Mandelstein | G06F 16/27 |
| | | | 707/E17.014 |
| 2014/0164357 A1* | 6/2014 | Collins | G06F 16/24532 |
| | | | 707/719 |
| 2014/0172775 A1* | 6/2014 | Niehoff | G06F 16/284 |
| | | | 707/600 |
| 2014/0172827 A1* | 6/2014 | Nos | G06F 16/2423 |
| | | | 707/722 |
| 2014/0279839 A1* | 9/2014 | Balzar | G06F 16/20 |
| | | | 707/607 |
| 2014/0280939 A1* | 9/2014 | Banatwala | H04L 63/20 |
| | | | 709/225 |

(Continued)

*Primary Examiner* — Tony Mahmoudi
*Assistant Examiner* — Kamal K Dewan
(74) *Attorney, Agent, or Firm* — Standley Law Group LLP; Jeffrey S. Standley; Adam J. Smith (57) ABSTRACT

A multidimensional multitenant system comprises a database storing objects comprising elements that are contributed by tenants belonging to one of a plurality of tenant types. Objects with elements contributed by tenants of a given tenant type are isolated from objects with elements contributed by other tenants of that type. Users of a tenant have access to data that includes elements contributed by tenants of other types.

15 Claims, 9 Drawing Sheets

Environment 110

(56) References Cited

U.S. PATENT DOCUMENTS

| | | | | |
|---|---|---|---|---|
| 2016/0203157 A1* | 7/2016 | Kuruganti | ............... | G06F 16/27 |
| | | | | 726/4 |
| 2016/0253461 A1* | 9/2016 | Sohr | ....................... | C25B 11/04 |
| | | | | 705/3 |
| 2016/0371315 A1* | 12/2016 | Kwon | .................... | G06F 16/211 |
| 2017/0235466 A1* | 8/2017 | Tanwir | .................. | G06F 3/0481 |
| | | | | 715/738 |
| 2017/0364345 A1* | 12/2017 | Fontoura | .................... | G06F 9/52 |
| 2018/0181720 A1* | 6/2018 | Ensey | .................... | G16H 50/20 |
| 2019/0095241 A1* | 3/2019 | Ago | .................. | G06F 16/24573 |
| 2019/0095534 A1* | 3/2019 | Levine | ............... | G06F 16/9038 |
| 2019/0286832 A1* | 9/2019 | Szeto | ..................... | H04L 63/102 |
| 2019/0325039 A1* | 10/2019 | Fernando | .................. | G06F 9/54 |
| 2019/0340282 A1* | 11/2019 | Zimmermann | ..... | G06F 16/2282 |
| 2019/0372766 A1* | 12/2019 | Bahrenburg | ............ | G06F 21/44 |
| 2020/0028795 A1* | 1/2020 | Tiwary | ............. | G06Q 10/06313 |
| 2020/0125455 A1* | 4/2020 | Neelakanteshwar | ........................ | |
| | | | | G06F 9/4451 |
| 2020/0125542 A1* | 4/2020 | Purushothaman | .... | G06F 16/211 |
| 2021/0117380 A1* | 4/2021 | Fernando | ............. | G06F 16/162 |
| 2021/0248125 A1* | 8/2021 | Kwon | .................. | G06F 16/211 |

* cited by examiner

| col_A | tt1 | tt2 | tt1_f1 | tt2_f1 |
|---|---|---|---|---|
| X | tt1_1 | tt2_1 | 1.1.1 | 2.1.1 |

702

| col_B | tt2 | tt2_f2 |
|---|---|---|
| X | tt2_2 | 2.2.1 |

703

| tt1 | tt2 | tt1_f1 | tt2_f1 | tt2_f2 |
|---|---|---|---|---|
| tt1_1 | ? | 1.1.1 | 2.1.1 | 2.2.1 |

MULTIDIMENSIONAL MULTITENANT SYSTEM

BACKGROUND

The disclosure relates to multitenant systems in general and more specifically to a multidimensional multitenant system that stores objects comprising data contributed by multiple tenants and allows multiple tenants to access elements of an object.

A multitenant database hosts data provided by tenants. Each tenant represents an organization that represents a group of users who may have access to the data provided by the tenant, subject to the authorization rules of the tenant. The multitenant database divides data into subsets such that only one tenant may access a subset of data. In this way, the multitenant database allows for sharing of resources while keeping tenant data isolated from other tenants, increasing privacy of potentially sensitive data. For example, a single database may be shared by multiple organizations or the same application may be executed by multiple tenants.

However, organizations rarely work in complete isolation. If one organization owns data that another organization needs to access, the owner organization needs to provide the data to the other organization. This may be done via email, file transfer, or any other method of transfer. For this, the data needs to be explicitly copied to the data storage of any other organizations that needs to process the data.

As a result, multiple copies of the same data are made. For example, an organization may have to provide access to a document to other organizations. Conventional multi-tenant systems require the organization to send a separate copy of the document to each system of the other organizations. As a result, communication and computing resources are wasted as a result of making copies of data and transmitting the data via a computer network. Accordingly, conventional multitenant systems perform inefficient resource utilization for several applications.

SUMMARY

A multidimensional multitenant system stores objects that combine elements contributed by tenants of a plurality of tenant types. Each element of an object is contributed by at most one tenant of a particular tenant type. Specifically, users of a tenant of one tenant type have access to objects contributed by that tenant but not to objects contributed by other tenants of the same tenant type.

The multidimensional multitenant system stores metadata describing tenants. The multidimensional multitenant system stores a plurality of objects for each tenant. Each object has a plurality of elements. The plurality of elements comprise subsets of elements, wherein each subset of elements is contributed by a tenant of a distinct tenant type. The multidimensional multitenant system receives from a first user associated with a first tenant of a first tenant type, a request to create an object. The multidimensional multitenant system creates the object according to the request. The multidimensional multitenant system receives another request to update an element of an object from a second user of a second tenant of a second tenant type. The multidimensional multitenant system performs the update according to the other request. The multidimensional multitenant system receives a third request to access the object from a user associated with the first tenant. The multidimensional multitenant system sends elements of the updated object to the user associated with the first tenant. Accordingly, the multidimensional multitenant system allows multiple tenants to update elements of the same object and allows them to access the updates to the object.

In an embodiment, the multidimensional multitenant system stores metadata representing an association between each element of the object and a tenant of a tenant type. The multidimensional multitenant system stores, for each element of an object, metadata describing a type of access allowed to the element by a tenant, for example, read access, write access, controller access, unrestricted access, or no access.

In an embodiment, the multidimensional multitenant system performs coordination between multiple tenants associated with an object to determine whether an operation such as create or delete can be performed on the object. The multidimensional multitenant system receives a request to perform an operation on the object. The multidimensional multitenant system receives a ratification status of the operation from each tenant contributing to the object. The multidimensional multitenant system determines whether the operation is performed based on the ratification status received from each tenant contributing to the object. The ratification status is selected from a plurality of status values including: pending, ratified, and vetoed. If a ratification status value indicates a pending status, the multidimensional multitenant system waits for the ratification status value for the tenant to change. If the ratification status values indicate a ratified status from all the tenants contributing to the object, the multidimensional multitenant system performs the requested operation. If the ratification status values indicate a vetoed status from any one of the tenants contributing to the object, the multidimensional multitenant system rejects the requested operation.

In an embodiment, the multidimensional multitenant system combines objects to create new objects. The multidimensional multitenant system receives a request to perform an operation that creates one or more new objects. Each new object is obtained by combining a plurality of objects. The multidimensional multitenant system executes the operation to create the one or more objects by conforming to the following rules: (1) a tenant controlling a particular element controls a corresponding element in the new object, and (2) at most one tenant of any tenant type is a controlling tenant for any element in the new object.

The features and advantages described in the specification are not all inclusive and in particular, many additional features and advantages will be apparent to one of ordinary skill in the art in view of the drawings, specification, and claims. Moreover, it should be noted that the language used in the specification has been principally selected for readability and instructional purposes, and may not have been selected to delineate or circumscribe the disclosed subject matter.

BRIEF DESCRIPTION OF DRAWINGS

The disclosed embodiments have other advantages and features which will be more readily apparent from the detailed description, the appended claims, and the accompanying figures (or drawings). A brief introduction of the figures is below.

Reference will now be made in detail to several embodiments, examples of which are illustrated in the accompanying figures. It is noted that wherever practicable similar or like reference numbers may be used in the figures and may indicate similar or like functionality. The figures depict embodiments of the disclosed system (or method) for purposes of illustration only. One skilled in the art will readily recognize from the following description that alternative embodiments of the structures and methods illustrated herein may be employed without departing from the principles described herein.

DETAILED DESCRIPTION

Organizations have traditionally used separate systems to manage their data. Within a vertical industry or horizontal business function, there has been a migration from physically separate, on-premise systems to logically separate, but physically shared, multi-tenant systems.

Interactions between organizations are typically performed using a variety of mechanisms such as email, messaging, electronic data interchange (EDI), file transfer, and even manual data entry to transmit data from one system to another. The resultant duplication of data, delay, and frequency of errors impedes efficiency and analysis of the overall ecosystem of organizations that interact closely, such as companies that specialize in materials, design, manufacturing, marketing and distribution.

When the interactions between the organizations participating in an ecosystem are sufficiently well-understood and uniform, a multidimensional multitenant system enables the data of entire ecosystems to be consolidated into a single logical database known as a multidimensional multitenant system. The multidimensional multitenant system provides controlled access to data belonging to organizations of different tenant types while keeping the data belonging to organizations of the same tenant type separate. Each data element is created and managed by an organization of the appropriate tenant type. That data can then be shared with organizations of other tenant types. To ensure isolation between tenants, data that is controlled by a tenant of a given tenant type can only be accessed by one tenant of the given tenant type. Data that is not explicitly shared with tenants of a given tenant type is accessible to all tenants of that tenant type (i.e., access to that data is not restricted to any specific tenant of that tenant type). In an embodiment, the multidimensional multitenant system stores a flag indicating whether access is "unrestricted." Unrestricted access specifies that all tenants of a tenant type may access that data. For example, if a data element is specified as having "read" access for a tenant type with "unrestricted" flag set, all tenants of that tenant type are allowed to access the element. Such access may be used for publishing information, for example, for sharing documents such as public catalog or system reference data. In an embodiment, the ability to specify unrestricted access is limited to privileged tenants, for example, only a system tenant is allowed to specify unrestricted access. The multidimensional multitenant system may place additional limitation on unrestricted create, update, and delete access, for example, by disallowing them or performing additional checks/confirmation if a tenant specifies these types of access for an element.

Because tenants share the same copy of data they are entitled to access, a multidimensional multitenant system eliminates redundant storage, transmission delays and transcription errors. Therefore, an entire community of organizations can conduct their operations using applications integrated to a common database. A multidimensional multitenant system improves computing efficiency and storage efficiency for organizations since they no longer need to use various data transfer mechanisms as if the data was stored in completely independent data systems. By maintaining and sharing single copy of data, the multidimensional multitenant system further eliminates storage of stale copies of data.

Given a set of N tenant types and tenants of each tenant type, a multidimensional multitenant system can be considered an N-dimensional space where each vector of tenants identifies a collection of data. For vectors of length N, the collection of data is a point in the space. This point represents the set of all data contributed collectively, by the specified tenants. For vectors of length N-i, the data is a plane, or high-dimensional volume, containing all the data and only the data accessible to the tenants of the vector. A tenant has access to any such collection where the tenant is one of the tenants in the vector. The traditional multitenant system has vectors of length N=1 with a single tenant type, while the multidimensional multitenant system contains multiple tenant types.

Overall System Environment

Figure 1:
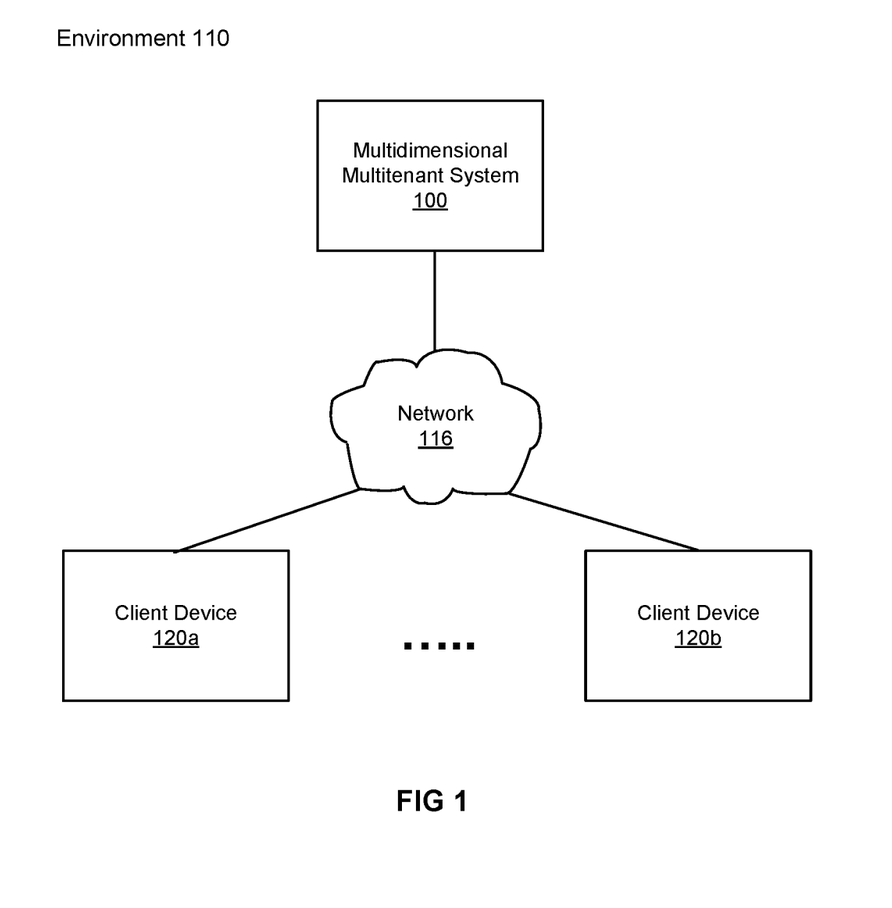
FIG. 1 shows the overall system environment for a multidimensional multitenant system, according to an embodiment.

FIG. 1 shows the overall system environment of the multidimensional multitenant system, according to an embodiment. FIG. 1 shows various systems involved in generation of and processing of data. The overall system environment includes a multidimensional multitenant system 100, a network 116, and one or more client devices 120. In other embodiments, more or fewer systems/components than those indicated in FIG. 1 may be used. A user may interact with the multidimensional multitenant system via the client device 120 through the network 116. A user is associated with a tenant. Furthermore, there may be more or fewer instances of each system shown in FIG. 1, such as the client device 120.

A multidimensional multitenant system has more than one tenant type, and objects may combine elements contributed by multiple tenants, but at most one of each tenant type. Objects that have elements contributed by a tenant of a given tenant type are isolated from objects with elements contributed by all other tenants of that tenant type. Specifically, users belonging to a tenant have access to objects contributed, in whole or in part, to that tenant, and do not have access to data contributed, in whole or in part, by any other tenant of the same tenant type. Objects may also be referred to herein as records and each element of the object be referred to as a field. An object may also be referred to as an entity and each element of the object referred to as an attribute. An object map be stored as rows of one or more tables and each element stored as a column.

The multidimensional multitenant system 100 enables each element in an object to be associated with up to one tenant type. This tenant type is called the controller of the field. An object that has one or more elements controlled by a tenant type has a tenant of that type that, directly or indirectly, controls operations on those elements, including, but not limited to: create, read, update, delete, search, index, define triggers, store procedures, store constraints, and include in views.

The logical database schema may include one or more tenant types as contributors to an object. In an embodiment, the only data contributed to the object from a tenant of a tenant type may be the identity of the tenant of that tenant type. In other words, a tenant may not control any element of an object. The logical database schema therefore enables other contributors to create objects that are specific to tenants of tenant types that do not contribute anything to the objects other than their identities. In another embodiment, the logical schema database may also omit one or more tenant types as contributors to an object, giving tenants of that tenant type unrestricted access to those objects. Additional metadata may be used to restrict the access of omitted tenant types. For example, tenants of one omitted tenant type could be read-only, while tenants of another omitted tenant type could be no-access.

Users belonging to a tenant have access to data that includes elements contributed by tenants of other tenant types. The logical database schema defines a fixed collection of tenant types, and enables each element, or field, in an object to be associated with up to one tenant type, called the controller of the field. Each instance of an object that has one or more elements controlled by a tenant type has a tenant of that tenant type which controls, either directly or indirectly, all operations on those elements of the instance, including but not limited to: create, read, update, delete, search, index, definition of triggers, stored procedures, constraints, and inclusion in views.

The logical schema may include one or more tenant types as contributors to an object even if the only data contributed to the object is the identities of tenants of those tenant types. This enables the other contributors to create objects which are specific to tenants of tenant types which do not contribute to those objects anything other than their identities.

Users of all tenant types expect their data to not be exposed to organizations (tenants) of the same tenant type. Just as organizations (tenants) in a traditional multi-tenant database expect their data to be isolated from other tenants, organizations of the same tenant type in a multidimensional multitenant system expect their data to be isolated from other organizations of the same tenant type. In a multidimensional multitenant system, tenants of a given tenant type expect to have access to related data belonging to tenants of other tenant types. The notion of "related data" means, within a tenant of a given tenant type, the tenants of other tenant types are isolated from each other. For example, in a health care database, a provider's clinical data for one patient is isolated from clinical data for all other patients. Similarly, data from an insurance provides is isolated from data of all other insurance providers.

FIG. 1 and the other figures use like reference numerals to identify like elements. A letter after a reference numeral, such as "120a," indicates that the text refers specifically to the element having that particular reference numeral. A reference numeral in the text without a following letter, such as "120," refers to any or all of the elements in the figures bearing that reference numeral (e.g. "120" in the text refers to reference numerals "120a" and/or "120b" in the figures).

System Architecture of the Multidimensional Multitenant System

Figure 2:
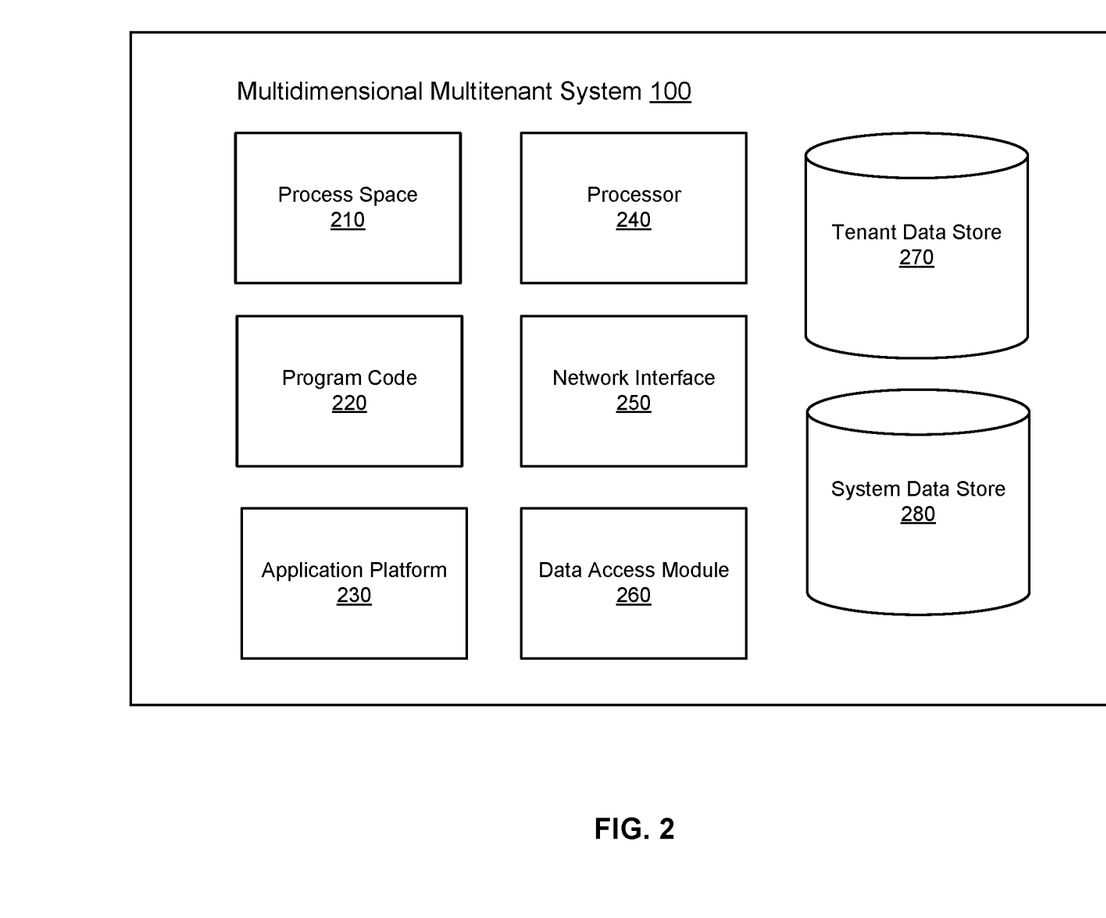
FIG. 2 shows the system architecture for the multidimensional multitenant system, according to an embodiment.

FIG. 2 shows the modules of the multidimensional multitenant system 100, the modules including: a process space 210, a program code 220, an application platform 230, a processor 240, a network interface 250, a data access module 260, a tenant data store 270, and a system data store 280. This is one embodiment of the multidimensional multitenant system, and in other embodiments, there may be more or fewer modules.

The process space 210 contains the set of processes running within the multidimensional multitenant system 100. The processes are for the tenants and for the multidimensional multitenant system 100, according to an embodiment. The program code 220 implements various functions of the multidimensional multitenant system 100. The application platform 230 includes an application setup mechanism to support applications developed for the multidimensional multitenant system.

Applications and processes run on the processor 240. The processor also runs the program code 220 to implement the functions. The network interface 250 may send data via the network 116. The network interface 250 may convert the data into bits or different forms to send the data over the network 116. The data access module 260 accesses data stored in the tenant data store 270 and the system data store.

The tenant data store 270 stores the data associated with each tenant in the multidimensional multitenant system 100. The data is stored within the data store such that the data of different tenants are separate from one another. The system data store 280 stores information describing the different tenant type sand tenants and stores the metadata associated with the tenants and the data.

The various modules shown in FIG. 2 may interact via a network (not shown in the figure.) The network enables communications between the various systems. In one embodiment, the network uses standard communications technologies and/or protocols. In another embodiment, the entities can use custom and/or dedicated data communications technologies instead of, or in addition to, the ones described above. Depending upon the embodiment, the network can also include links to other networks such as the Internet.

Implementation of Multidimensional Multitenant System

Figure 3:
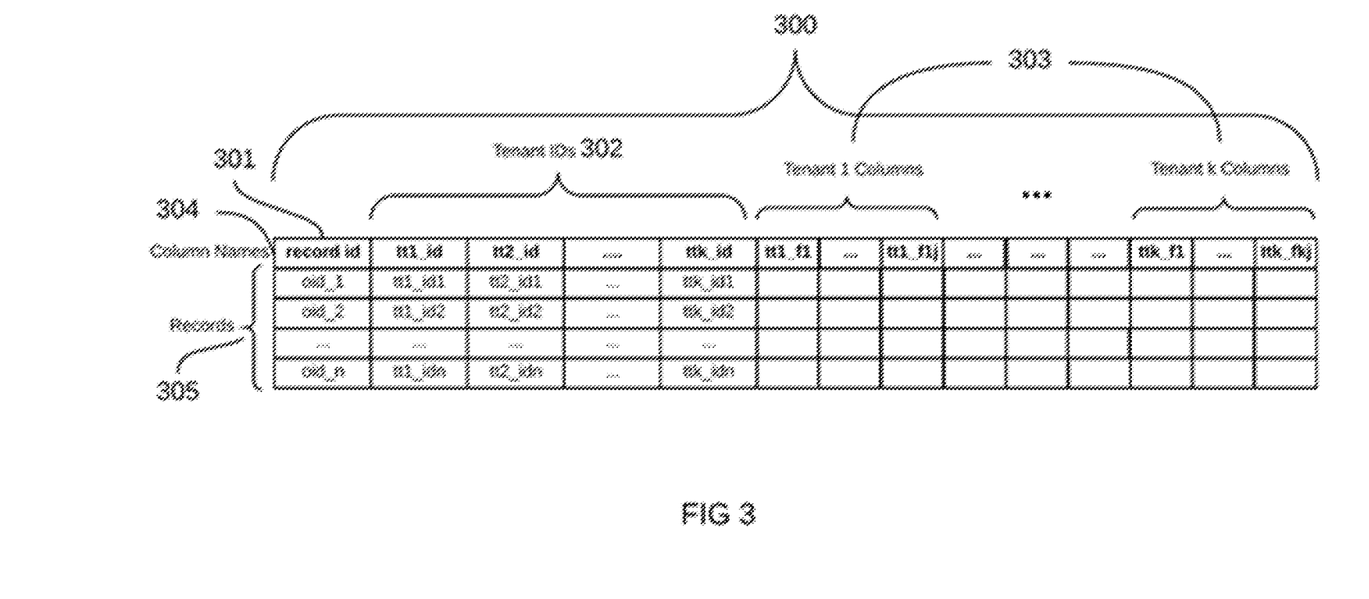
FIG. 3 illustrates representation of data in an implementation of the multidimensional multitenant system, according to an embodiment.

FIG. 3 illustrates representation of data in an implementation of the multidimensional multitenant system, according to an embodiment. The representation of data comprises one or more tables 300, each table storing records (or objects) 305. The objects 305 are represented as rows of the table 300. The table 300 has column names 304. The data comprises, for each object, a unique record identifier 301, one or more tenant identifiers 302, and one or more columns 303 corresponding to each tenant identifier. The columns represent elements of the object. Each tenant type tti has corresponding columns tti_f1 through tti_fij, where ij is the number of columns (or fields or elements) belonging to the tenants of tenant type tti. The table 300 has at most one tenant identifier for each tenant type tt1 through ttk. Accordingly, each element of an object is associated with only one tenant of a particular tenant type. The tenant of a particular tenant type associated with an element is called the contributor of that element.

The object identified by object identifier 301 oid_u combines data contributed by tenants ttv_idu, for v between 1 and k, inclusive, each a member of the corresponding tenant type ttv. Each tenant ttv_idu controls the columns ttv_fw for w between 1 and vj, inclusive. Control of a column or element means that the controlling tenant can perform all create, read, update, delete, and search operations on that column, unless forbidden by constraints that might be imposed by the database schema according to rules not specified here.

Different tenants (i.e., tenants ttv_idx, where x is different from u) of the same tenant type ttv do not have any access to any part of any object controlled by ttv_idu. This condition guarantees the isolation of data belonging to different tenants of the same tenant type. Tenants tty_idu of different tenant types tty, which contribute to the object oid_u, have access to the fields ttv_fw according to access controls described in FIG. 4.

Figure 4:
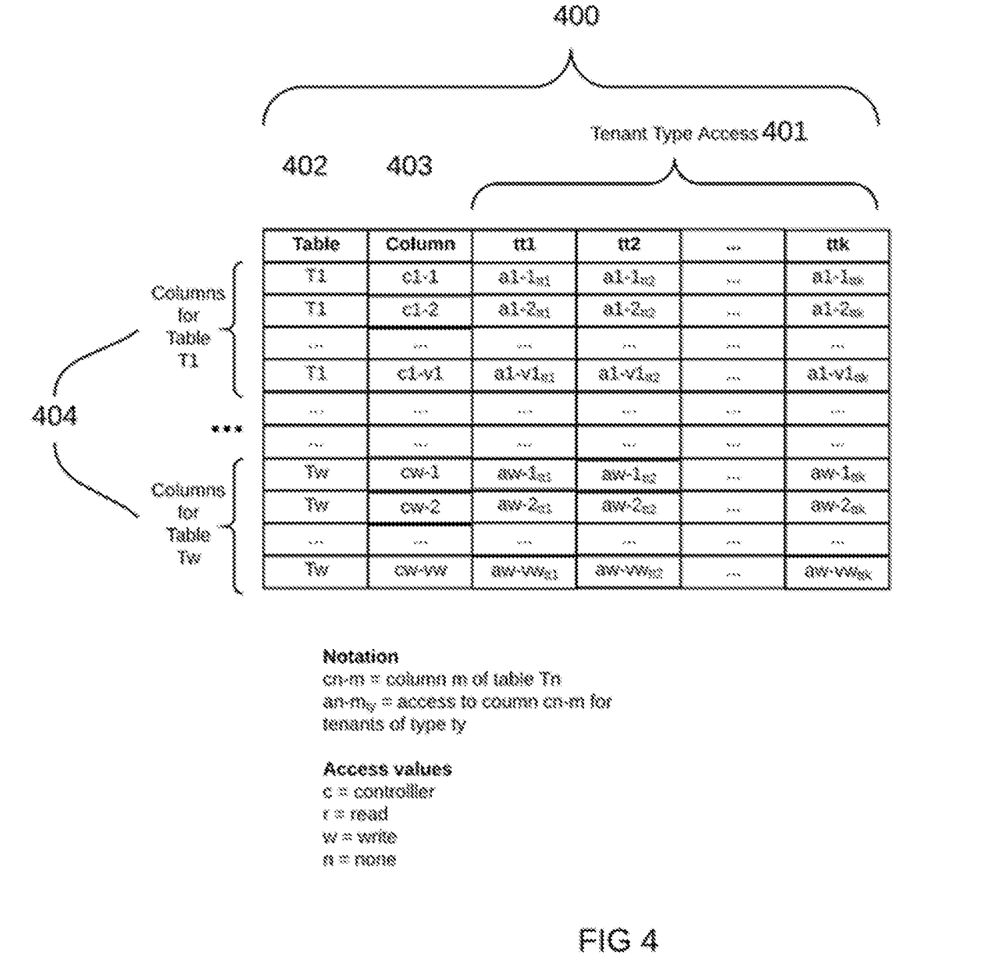
FIG. 4 illustrates metadata specifying access to the elements of objects in the multidimensional multitenant system, according to an embodiment.

FIG. 4 illustrates metadata specifying access to the elements of objects in the multidimensional multitenant system, according to an embodiment. The metadata can be represented in a metadata table 400 according to one embodiment. In this embodiment, objects are represented by rows of tables like the one in FIG. 3. Each metadata table 400 represents some or all of the elements of one or more tenant types of object. As illustrated in FIG. 4, the metadata table 400 has a row for each column 403 of each object table 402. The tenant type access columns 401 of that row specify the access permitted to the element represented by that column for tenants of each tenant type tti, for i between 1 and k.

Since the metadata table 400 allows only one element to be stored for each tenant type for a given element (column) of an object, only one tenant of that tenant type is allowed the specified access to the element. For each element (or field or column) cu-v of table Tw, the values au-v$_{tti}$ in column tti of the corresponding row specify the access values for that element. In an embodiment, the access values are C for controller, R for read, W for write, and N for none. Other embodiments may use other access values.

Each element of an object has exactly one controller tenant of a particular tenant type. Accordingly, for exactly one tenant type tto, where o is between 1 and k, the value au-v$_{tto}$ is C, indicating that the tenant of tenant type tto is the controller of the field cu-v. The tenant of tenant type tto is the value in the column tto_id of the corresponding table Tu.

The controller, C, can perform any and all operations on the element. A tenant with read permission, R, may read the value in that element, but may not write (update) the element. A tenant with write permission, W, may both read and write the value in the element. A tenant with access value "none," N, may neither read nor write the value in the element.

Other embodiments may use different access codes, including arbitrary computable constraints on the values that may be written, permissions to set null values, and the like.

Coordinating Operations on Objects

In some embodiments, the multidimensional multitenant system allows coordination of operations based on input received from each tenant that contributed to an object. The multidimensional multitenant system receives a request to perform an operation on the object. The request may be received from a tenant that contributes to the object. The request may include provisional values for elements of the object that are controlled by other tenants. The operation is selected from a plurality of operation types comprising a create operation type and a delete operation type. The multidimensional multitenant system receives a ratification status for the operation from each tenant contributing to the object. The multidimensional multitenant system determines whether the operation is performed based on the ratification status received from each tenant associated with the object.

In an embodiment, the ratification status is selected from a plurality of status values comprising pending, ratified, and vetoed. The multidimensional multitenant system initializes the ratification status for the tenant that initiates the operation as ratified and the ratification status for all other tenants as pending. If the multidimensional multitenant system determines that the ratification status value for any one of the tenants contributing to the object indicates a pending status, the multidimensional multitenant system waits for the ratification status value for the tenant to change before making a decision on whether to perform the operation or not. As part of ratification, a tenant may set values for the elements it controls. It may accept any provisional values for those elements and override them, and it may set values for any of the elements it controls that do not have provisional values. If the multidimensional multitenant system determines that the ratification status values from all tenants contributing to the object indicate a ratified status, the multidimensional multitenant system performs the operation on the object. If the multidimensional multitenant system determines that the ratification status value from any one tenant contributing to the object indicates a vetoed status, the multidimensional multitenant system rejects the request to perform the operation on the object.

Figure 5:
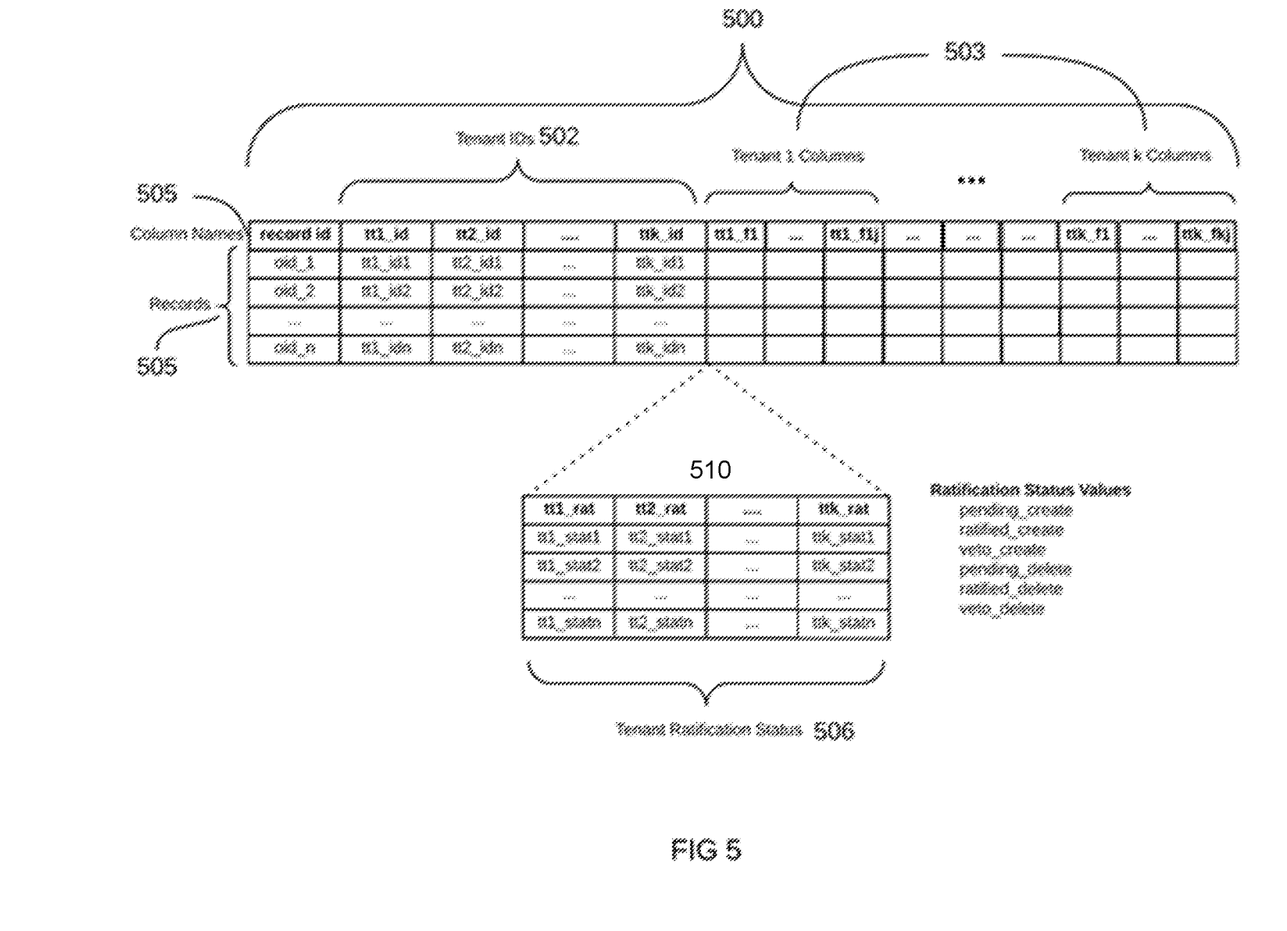
FIG. 5 illustrates an example of metadata stored for coordinating operations among the tenants contributing to an object.

FIG. 5 illustrates an example of metadata stored for coordinating operations among the tenants contributing to an object. Per the embodiment of FIG. 4, FIG. 5 shows the ratification columns 506 in the object table 500 that corresponds to object table 400 of FIG. 4. The table 500 comprises records 505 storing data for objects. The table stores tenant IDs 502 and tenant columns 503 corresponding to the tenants identified by the tenant IDs 502. The ratification columns 500 indicate the tenant ratification status 506 of the operation for each contributing tenant.

Combining Objects

Figure 6:
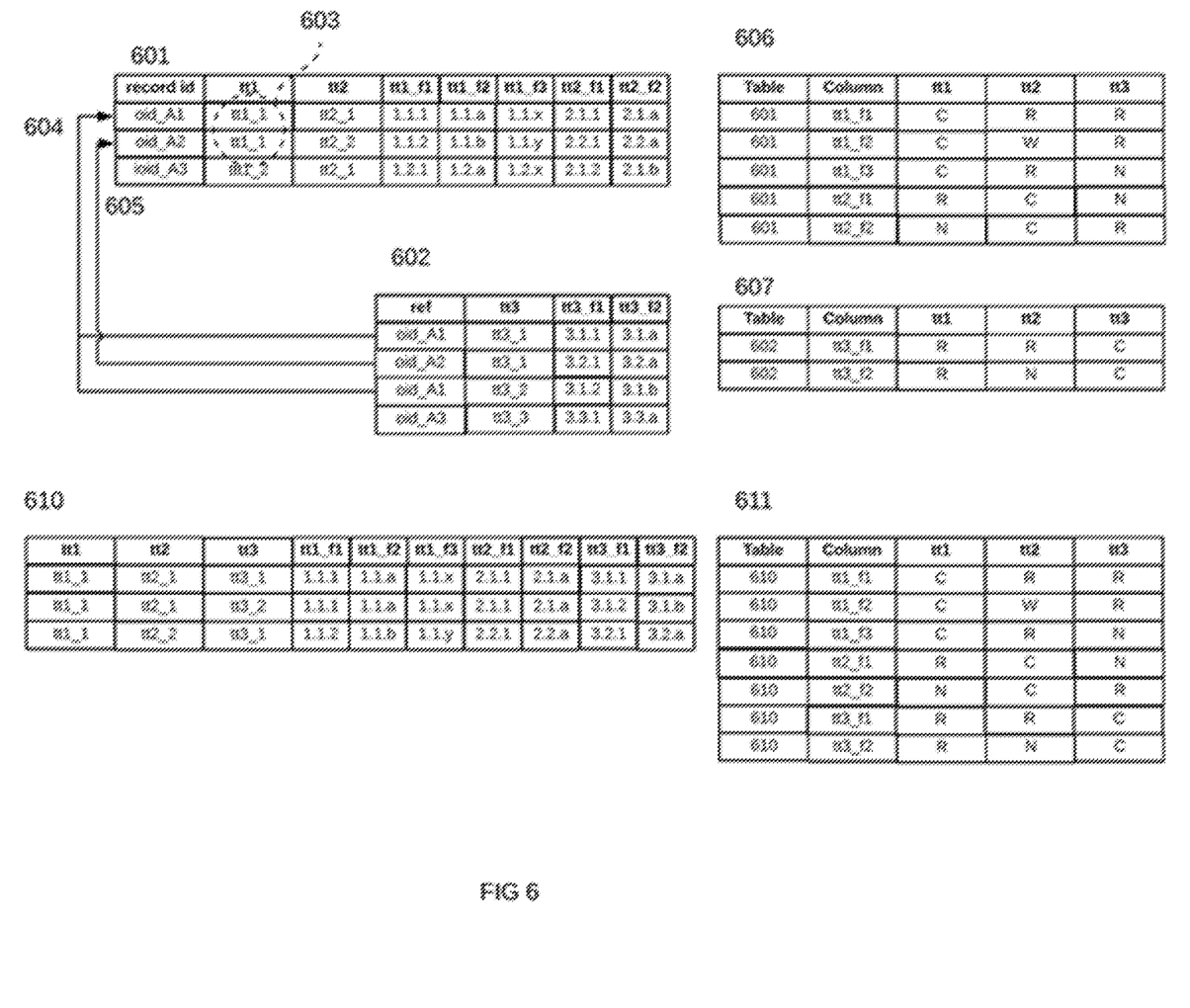
FIG. 6 shows an example illustrating combination of objects comprising elements controlled by different sets of tenant types, according to an embodiment.

In some embodiments, the multidimensional multitenant system combines objects to generate new objects. FIG. 6 shows an example illustrating a combination of objects comprising elements controlled by different sets of tenant types, according to an embodiment. The multidimensional multitenant system ensures that the following two rules are not violated when objects are combined to generate new objects. First, the multidimensional multitenant system ensures that a tenant of a particular tenant type that controls any contributing element controls the corresponding element in the new object resulting from the combination. Second, the multidimensional multitenant system ensures that at most one tenant of any tenant type can be a controlling tenant for any element in the combination. The first rule ensures that no tenant loses control of its data when it is combined with other data. The second rule ensures that the combination is consistent, in the sense that data from one tenant of a given tenant type is not mixed with data from another tenant of the same tenant type, which would violate isolation.

Any method of combining data may be used as long the method follows the two rules, for example, join of sets of objects, union of sets of objects, intersection of sets of objects, and so on. FIG. 6 shows an embodiment of a relational database, and the method of combining data uses a foreign key reference from the "ref" column of table 602 to the primary key column "record id" of table 601, which corresponds to an object identifier. The combination of table 602 and table 601, combination table 610, is the relational join of the two tables on those columns where the tenant of tenant type tt1_id is tt1_1. The restriction of tt1_id to a single value–tt1_1 illustrates a combination built for the tenant tt1_1. If a rule is violated, the operation fails and the result is not displayed since this would violate isolation. In an embodiment, an error is displayed indicating a violation of the rule without actually displaying the data values.

In an embodiment, the multidimensional multitenant system does not enforce the above rules if the temporary result is not exposed to any tenant. For example, the multidimensional multitenant system may compute a query result set by joining tables without tenant constraints and then filtering to select the rows for the specified tenants. Accordingly, the multidimensional multitenant system does not enforce the rules on the intermediate unfiltered join if the intermediate join result is not exposed to any tenant. However, if the intermediate result table were exposed to a tenant, for example, if the tenant is allowed to save the intermediate results in a table and view them, the multidimensional multitenant system enforces the rules, for example, by causing the statement to store the intermediate results to fail. In an embodiment, the multidimensional multitenant system allows a user with special privilege to view the intermediate results without enforcing the above rules, for example, a support engineer may be allowed to review the result for debugging purposes.

The access metadata for table 601 is shown in table 606, and the access metadata for table 602 is shown in table 607. The access metadata for the combination table 610 is shown in table 611. In this embodiment, the access codes for all elements for all tenant types are preserved in the combination. In other embodiment, the multidimensional multitenant system receives with the combination method, rules (or policies) defined by each tenant type that change the access codes for elements controlled by that tenant type.

Figure 7:
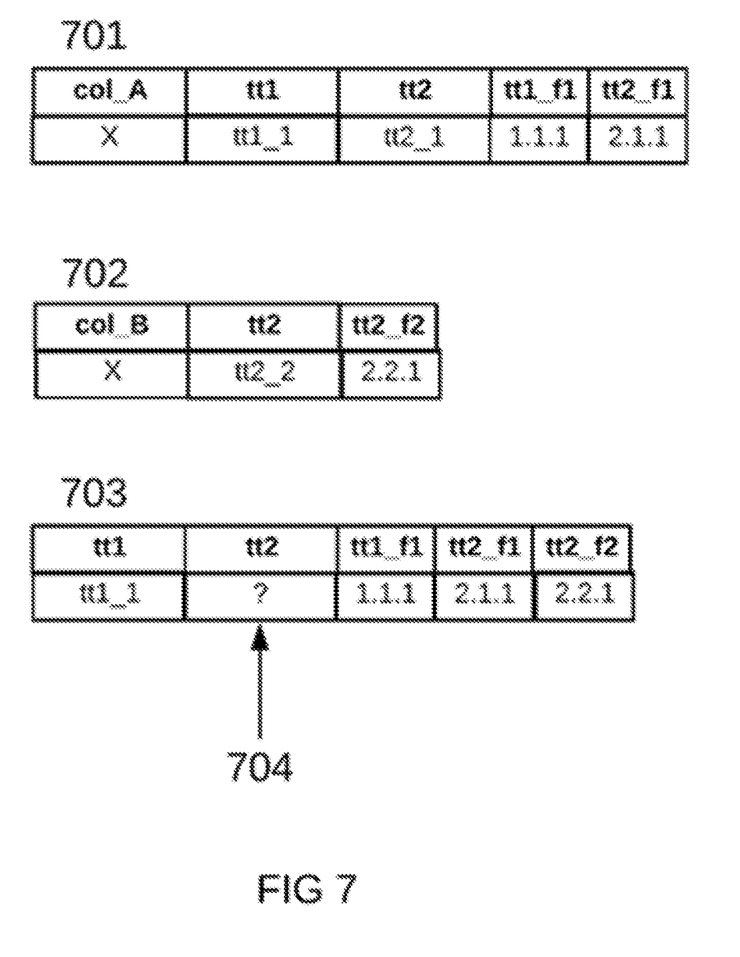
FIG. 7 illustrates an example of a data combination that violates a combination rule, according to an embodiment.

FIG. 7 illustrates an example of a data combination that violates a combination rule, according to an embodiment. Combination table 703 is built by selecting columns tt1_f1 and tt2_f1 from table 701 and column tt2_f2 from table 702, where col_A of table 701 is equivalent to col_B of table 702. By the first rule, column tt2_f1 in the combination 703 must be controlled by tt2_1, and column tt2_f2 must be controlled by tt2_2. However, by the second rule, only one tenant of tenant type tt2 can control any element, so this combination is not allowed and the multidimensional multitenant system causes this combination operation to fail.

Overall Process

Figure 8:
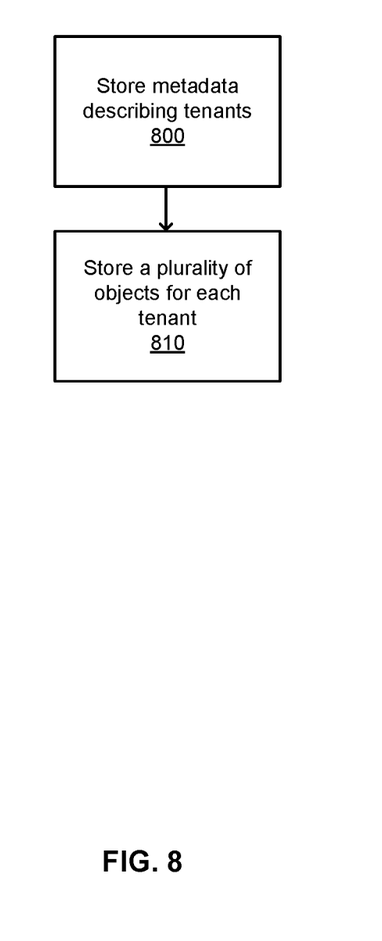
FIG. 8 illustrates the process of storing data in the multidimensional multitenant system 100, according to one embodiment.

FIG. 8 illustrates the process of storing data in the multidimensional multitenant system 100, according to one embodiment. The multidimensional multitenant system 100 first stores 800 metadata describing tenants of the multidimensional multitenant system 100. Each tenant stored is associated with a set of users. In addition, each tenant may be of a tenant type from a plurality of possible tenant types.

The multidimensional multitenant system 100 then stores 810 a plurality of objects for each tenant. Each object may have a plurality of elements. The plurality of elements comprises a plurality of subsets of elements. Each subset of elements is contributed to by a tenant of a distinct tenant type. As a result, each element of the object is associated with a single tenant of a tenant type.

Figure 9:
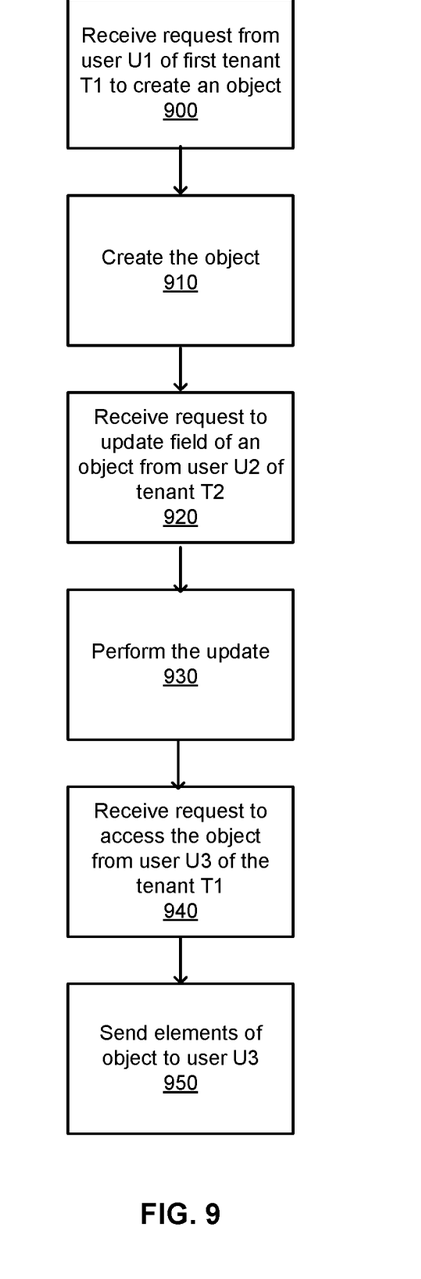
FIG. 9 illustrates the process of storing and accessing data by tenants of different tenant types, according to one embodiment.

FIG. 9 illustrates the process of storing and accessing data by tenants of different tenant types, according to one embodiment. The multidimensional multitenant system 100 receives 900 a request from a user U1 of a tenant T1 to create an object and creates 910 the object, according to the request. The tenant T1 is of a tenant type TT1. The multidimensional multitenant system 100 receives 920 a request from a user U2 of a tenant T2 to update an element of an object and performs 930 the update. The tenant T2 is of a tenant type TT2 different than the tenant type TT1.

The multidimensional multitenant system receives 940 a request to access the object by a third user U3 who is of the tenant T1, the same tenant as the user U1. The multidimensional multitenant system 100 sends 950 elements of the object to the user U3. The elements of the object were those updated responsive to the request from the second user. Accordingly, users of tenant T1 of type TT1 and tenant T2 of type TT2 are able to access elements of an object and a user of tenant T1 of type TT1 is able to access data modified by a user of tenant T2 of type TT2.

Applications

The multidimensional multitenant system is useful in many domains where multiple independent organizations or groups of users need to interact. In the healthcare domain, for example, the ecosystem consists of patients (along with their families, caregivers, etc.), providers (hospitals, clinics, labs, etc.), and payers (primarily insurance companies). In a consolidated healthcare database, users have similar expectations of what data they should be able to access, but differing based on the tenant type of their organization.

A user at a hospital expects to have access to clinical, claims, and personal data for the hospital's patients. Clinical data and claims would be restricted to data created by the user's hospital. A HIPAA consent from the patient could allow access to clinical data from other providers. Also, each tenant type of organization has its own access control, using mechanisms such as role-based access control. Such controls apply to individual users, not organizations as a whole.

A user in a patient's circle expects to have access to the patient's clinical data and claims from all providers and payers. A comprehensive patient view is particularly important for analyzing data in order to improve the quality of care. Additionally, payor users expect to have access to their own claims and related clinical and patient data, across all providers.

The multidimensional multitenant system 100 provides access to patient clinical data and insurance claims to patients, providers, and payors, while also keeping data isolated from other patients and providers and payors not associated with the patient. This system can improve the efficiency of data sharing while still keeping patient data secure.

A healthcare information system combines data contributed by patients, providers, and payors. Each of these is a tenant type. A patient type tenant has users such as family members and caregivers as well as the individual patient. A provider type tenant has users such as doctors, nurses, pharmacists, billers, and administrators. A payor type tenant has users such as customer care specialists, analysts, and claims specialists.

Information about a patient typically combines data from the patient with one or more providers and payors. In a multidimensional multitenant database with these tenant types, the users belonging to a patient tenant have access to data from all providers and payors to which the patient tenant is a contributor, but no access to data for other patient tenants. The users for a provider tenant have access to data for all patients and payors to which the provider tenant is a contributor, but not to data for other provider tenants. Similarly, users for a payor tenant have access to data for all patients and providers to which the payor is a contributor, but not to data for other payors.

As an example, a record for a diagnostic test could contain the following information.

| Oid | Patient | Provider | Payor | Location | Date | Test | Doctor | Authorized |
|---|---|---|---|---|---|---|---|---|
| 123 | Pat Jones | Mercy Hospital | Humana | X Radio | Dec. 12, 2020 | MRI | Smith | Dec. 10, 2020 |

In this example, the patient contributes their preferred location and date for the test; the provider contributes the test to be performed and the doctor ordering the test; and the payor contributes the date the test was authorized.

The access metadata for this table would be as follows.

| Table | Column | Patient | Provider | Payor |
|---|---|---|---|---|
| Diagnostic Test | Location | C | R | N |
| Diagnostic Test | Date | C | R | N |
| Diagnostic Test | Test | R | C | R |
| Diagnostic Test | Doctor | R | C | R |
| Diagnostic Test | Authorized | R | R | C |

In this example, only the controller of any column can write it. All other contributing tenants may read columns they don't control, with the exception that the payor is not able to read the date and location chosen by the patient.

Another example shows more than one payor by normalizing the schema as follows. Following is a patient table.

| Oid | Patient | Provider | Location | Date | Test | Doctor |
|---|---|---|---|---|---|---|
| 123 | Pat Jones | Mercy Hospital | X Radio | Dec. 12, 2020 | MRI | Smith |

Following is an example provider table.

| DT | Payor | Authorized |
|---|---|---|
| 123 | Humana | Dec. 10, 2020 |
| 123 | Cigna | Dec. 11, 2020 |

The payors HUMANA and CIGNA would see the join rows for their respective authorizations, but not each other's, whereas the patient and provider would see both authorization dates.

Multidimensional multitenant systems have applications in other domains that require interactions between tenants of different tenant types. For example, another application for multidimensional multitenant system is a system that stores information for automobile insurance including tenants of tenant type users, tenants of tenant type insurers and tenants of tenant type automobile repair workshops. Objects stored in the system represent insurance claims, for example, insurance claims as a result of automobile accidents. The system may be extended to store objects representing other types of insurance claims for example, claims for property damages.

Another application for a multidimensional multitenant system is a system that stores data of various parties that interact with real estate transactions, for example, a system with tenants of tenant type home buyers, tenants of tenant type real estate agents, and tenants of tenant type loan providers. Objects stored in the system represent real estate transactions, for example, transactions representing buying and selling of houses.

Alternative Embodiments

It is to be understood that the Figures and descriptions of the present invention have been simplified to illustrate elements that are relevant for a clear understanding of the present invention, while eliminating, for the purpose of clarity, many other elements found in a multi-tenant system. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to such elements and methods known to those skilled in the art.

Some portions of the above description describe the embodiments in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like. Furthermore, it has also proven convenient at times, to refer to these arrangements of operations as modules, without loss of generality. The described operations and their associated modules may be embodied in software, firmware, hardware, or any combinations thereof.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. It should be understood that these terms are not intended as synonyms for each other. For example, some embodiments may be described using the term "connected" to indicate that two or more elements are in direct physical or electrical contact with each other. In another example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the invention. This description should be read to include one or at least one and the singular also includes the plural unless it is obvious that it is meant otherwise.

Upon reading this disclosure, those of skill in the art will appreciate still additional alternative structural and functional designs for a system and a process through the disclosed principles herein. Thus, while particular embodiments and applications have been illustrated and described, it is to be understood that the disclosed embodiments are not limited to the precise construction and components disclosed herein. Various modifications, changes and variations, which will be apparent to those skilled in the art, may be made in the arrangement, operation and details of the method and apparatus disclosed herein without departing from the spirit and scope defined in the appended claims.

We claim:

1. A method comprising:
   storing in a first table, by a multidimensional multitenant system, metadata describing tenants, wherein said metadata associates each tenant with a set of users, and each tenant with one of a plurality of tenant types;
   storing in a second table, by the multidimensional multitenant system, a plurality of objects for each tenant, each object having a plurality of elements comprising a plurality of subsets of elements, wherein each subset of elements is contributed to only by a tenant of a distinct tenant type, and wherein the plurality of objects are each contributed to by tenants of at least two distinct tenant types;
   receiving, from a first user associated with a first tenant of a first tenant type, a first request to create an object;
   creating the object in the second table according to the first request, the object comprising a plurality of elements;
   updating, in the first table, metadata describing, a plurality of tenants that contribute to elements of the object, the plurality of tenants comprising the first tenant of the first tenant type and a second tenant of a second tenant type, wherein the updated metadata describes that the first tenant has a specified access to a first element of the object and is an only tenant of the first tenant type allowed the specified access to the first element, and the second tenant is an only tenant of the second tenant type allowed specified access to a second element;
   based, at least in part, on a determination of a requesting user's tenant type from retrieved metadata describing the requesting user:
   preventing users of remaining tenants of the first tenant type from accessing the first element; and
   preventing users of remaining tenants of the second tenant type from accessing the second element;
   receiving a second request to update the second element of the object in the second table from a second user of the second tenant of the second tenant type;
   responsive to receiving the second request, accessing the first table to retrieve metadata describing the second tenant;
   determining whether the second tenant is allowed to update the second element of the object based on the retrieved metadata describing the second tenant, which includes an indication of the second tenant's tenant type;
   responsive to determining that the second tenant is allowed to update the second element of the object, retrieving a presaved ratification status value associated with update from each tenant of the plurality of tenants contributing to the object from the second table;
   responsive to retrieving the presaved ratification status value indicating a ratified status, performing an update to the object according to the second request;
   receiving a third request to access the object from a user associated with the first tenant;
   responsive to receiving the third request, accessing the first table to retrieve metadata describing the first tenant;
   determining whether the first tenant is allowed to access elements of the object based on the retrieved metadata describing the first tenant, which includes an indication of the first tenant's tenant type; and
   responsive to determining that the first tenant is allowed to access elements of the object, sending elements of the object including the first element and the second element to the user associated with the first tenant, the elements comprising the object updated responsive to the second request from the second user of the second tenant.

2. The method of claim 1, further comprising:
   storing in the first table by the multidimensional multitenant system, metadata representing an association between each element of the object and a tenant of a tenant type that contributes to the first element or the second element.

3. The method of claim 1, further comprising:
   for each element of an object, storing, in the first table by the multidimensional multitenant system, metadata describing a type of access to the first element or the second element of the object by a tenant of a tenant type that contributes to the corresponding first or second element.

4. The method of claim 3, wherein the type of access allowed to the first element or the second element of the object by the tenant of the tenant type is one of:
   a controller access,
   a read access,
   a write access,
   unrestricted access, or
   no access.

5. The method of claim 1, wherein the ratification status values are selected from a plurality of ratification status values comprising pending, ratified and vetoed, further comprising:
   responsive to a ratification status value indicting a pending status, waiting for the ratification status value for the tenant to change.

6. The method of claim 1, further comprising:
   responsive to receiving a ratification status value indicating a vetoed status from any of the plurality of tenants contributing to the object, rejecting the request to update the second element.

7. The method of claim 1, further comprising:
receiving a request to perform an operation that creates a new object obtained by combining a plurality of input objects; and
executing the operation to create the new object, wherein the combining comprises conforming to following rules:
a tenant controlling a particular element of an input object controls an element corresponding to the particular element in the new object, and
at most one tenant of any tenant type is a controlling tenant for any element in the new object.

8. The method of claim 1, further comprising:
receiving a fourth request to access the object from a user associated with a third tenant of the first tenant type; and
sending elements of the object to the user associated with the third tenant, the elements being those from the object other than the first element or the second element associated with the first tenant.

9. The method of claim 7, wherein the new object is obtained by performing one or more of a join of the plurality of objects, a union of the plurality of objects, or an intersection of the plurality of objects.

10. The method of claim 7, wherein the multidimensional multitenant system allows creation of the new object in spite of violating at least one of the rules if the new object represents a temporary result that is exposed to any tenant.

11. The method of claim 7, wherein multidimensional multitenant system causes creation of the new object to fail if one of the rules is violated if the new object represents a temporary result that is exposed to any tenant.

12. The method of claim 1, further comprising:
receiving a request to perform a combination operation that creates a combination table by selecting columns from a first table and a second table, wherein a column of the combination table includes data from a first column of the first table is controlled by a first tenant and the second column of the second table is controlled by a second tenant; and
responsive to determining that the column of the combination table would be controlled by both the first tenant and the second tenant, causing the combination operation to fail.

13. The method of claim 7, wherein a first tenant type represents patients, a second tenant type represents providers, and a third tenant type represents payers wherein the objects represent claim records, wherein the multidimensional multitenant system provides access to a claim record for a particular patient to a particular provider and a particular payer while isolating the claim record of the particular patient from providers other than the particular provider and payers other than the particular payer.

14. A non-transitory computer readable non-transitory storage medium storing instructions thereon, the instructions when executed by a processor cause the processor to:
store in a first table, by a multidimensional multitenant system, metadata describing tenants, wherein said metadata associates each tenant with a set of users, and each tenant with one of a plurality of tenant types;
store in a second table, by the multidimensional multitenant system, a plurality of objects for each tenant, each object having a plurality of elements comprising a plurality of subsets of elements, wherein each subset of elements is contributed to only by a tenant of a distinct tenant type, and wherein the plurality of objects are each contributed to by tenants of at least two distinct tenant types;
receive, from a first user associated with a first tenant of a first tenant type, a first request to create an object;
create the object in the second table according to the first request, the object comprising a plurality of elements;
update, in the first table, metadata describing, a plurality of tenants that contribute to elements of the object, the plurality of tenants comprising the first tenant of the first tenant type and a second tenant of a second tenant type, wherein the updated metadata describes that the first tenant has a specified access to a first element of the object and is an only tenant of the first tenant type allowed the specified access to the first element, and the second tenant is an only tenant of the second tenant type allowed specified access to a second element;
based, at least in part, on a determination of a requesting user's tenant type from retrieved metadata describing the requesting user:
prevent users of remaining tenants of the first tenant type from accessing the first element; and
prevent users of remaining tenants of the second tenant type from accessing the second element;
receive a second request to update the second element of the object in the second table from a second user of the second tenant of the second tenant type;
responsive to receiving the second request, access the first table to retrieve metadata describing the second tenant;
determine whether the second tenant is allowed to update the second element of the object based on the retrieved metadata describing the second tenant, which includes an indication of the second tenant's tenant type;
responsive to determining that the second tenant is allowed to update the second element of the object, retrieve a presaved ratification status value associated with update from each tenant of the plurality of tenants contributing to the object from the second table;
responsive to retrieving the presaved ratification status value indicating a ratified status, perform an update to the object according to the second request;
receive a third request to access the object from a user associated with the first tenant;
responsive to receiving the third request, access the first table to retrieve metadata describing the first tenant;
determine whether the first tenant is allowed to access elements of the object based on the retrieved metadata describing the first tenant, which includes an indication of the first tenant's tenant type; and
responsive to determining that the first tenant is allowed to access elements of the object, send elements of the object including the first element and the second element to the user associated with the first tenant, the elements comprising the object updated responsive to the second request from the second user of the second tenant.

15. A computer system, comprising:
a computer processor; and
a non-transitory computer readable non-transitory storage medium storing instructions thereon, the instructions when executed by the computer processor cause the computer processor to:
store in a first table, by a multidimensional multitenant system, metadata describing tenants, wherein said metadata associates each tenant with a set of users, and each tenant with one of a plurality of tenant types;

store in a second table, by the multidimensional multi-tenant system, a plurality of objects for each tenant, each object having a plurality of elements comprising a plurality of subsets of elements, wherein each subset of elements is contributed to only by a tenant of a distinct tenant type, and wherein the plurality of objects are each contributed to by tenants of at least two distinct tenant types;

receive, from a first user associated with a first tenant of a first tenant type, a first request to create an object;

create the object in the second table according to the first request, the object comprising a plurality of elements;

update, in the first table, metadata describing, a plurality of tenants that contribute to elements of the object, the plurality of tenants comprising the first tenant of the first tenant type and a second tenant of a second tenant type, wherein the updated metadata describes that the first tenant has a specified access to a first element of the object and is an only tenant of the first tenant type allowed the specified access to the first element, and the second tenant is an only tenant of the second tenant type allowed specified access to a second element;

based, at least in part, on a determination of a requesting user's tenant type from retrieved metadata describing the requesting user:
   prevent users of remaining tenants of the first tenant type from accessing the first element; and
   prevent users of remaining tenants of the second tenant type from accessing the second element;

receive a second request to update the second element of the object in the second table from a second user of the second tenant of the second tenant type;

responsive to receiving the second request, access the first table to retrieve metadata describing the second tenant;

determine whether the second tenant is allowed to update the second element of the object based on the retrieved metadata describing the second tenant, which includes an indication of the second tenant's tenant type;

responsive to determining that the second tenant is allowed to update the second element of the object, retrieve a presaved ratification status value associated with update from each tenant of the plurality of tenants contributing to the object from the second table;

responsive to retrieving the presaved ratification status value indicating a ratified status, perform an update to the object according to the second request;

receive a third request to access the object from a user associated with the first tenant;

responsive to receiving the third request, access the first table to retrieve metadata describing the first tenant;

determine whether the first tenant is allowed to access elements of the object based on the retrieved metadata describing the first tenant, which includes an indication of the first tenant's tenant type; and responsive to determining that the first tenant is allowed to access elements of the object, send elements of the object including the first element and the second element to the user associated with the first tenant, the elements comprising the object updated responsive to the second request from the second user of the second tenant.

* * * * *